US012484925B2

(12) United States Patent
Gras et al.

(10) Patent No.: US 12,484,925 B2
(45) Date of Patent: Dec. 2, 2025

(54) ULTRASONIC SURGICAL ASSEMBLY WITH AIR COOLING BROAD KNIFE AND IRRIGATION SLEEVE

(71) Applicant: Stryker European Operations Limited, Carrigtwohill (IE)

(72) Inventors: Guillaume Gras, Bienne (CH); Daniel Henderson, County Cork (IE); Conor McCarthy, County Cork (IE)

(73) Assignee: Stryker European Operations Limited, Carrigtwohill (IE)

( * ) Notice: Subject to any disclaimer, the term of this patent is extended or adjusted under 35 U.S.C. 154(b) by 274 days.

(21) Appl. No.: 18/268,279

(22) PCT Filed: Jun. 9, 2021

(86) PCT No.: PCT/IB2021/055077
§ 371 (c)(1),
(2) Date: Jun. 19, 2023

(87) PCT Pub. No.: WO2022/130035
PCT Pub. Date: Jun. 23, 2022

(65) Prior Publication Data

US 2024/0299059 A1 Sep. 12, 2024

Related U.S. Application Data

(60) Provisional application No. 63/197,773, filed on Jun. 7, 2021, provisional application No. 63/127,802, filed on Dec. 18, 2020.

(51) Int. Cl.
*A61B 17/32* (2006.01)

(52) U.S. Cl.
CPC ................. *A61B 17/320068* (2013.01); *A61B 2017/320074* (2017.08); *A61B 2017/320084* (2013.01)

(58) Field of Classification Search
CPC ........... A61B 17/320068; A61B 2017/320074; A61B 2017/320084
See application file for complete search history.

(56) References Cited

U.S. PATENT DOCUMENTS 5,324,299 A 6/1994 Davison et al.
5,449,370 A 9/1995 Vaitekunas
(Continued)

FOREIGN PATENT DOCUMENTS

EP 2760352 B1 7/2015
EP 2768403 B1 7/2015
(Continued)

OTHER PUBLICATIONS

English language abstract for EP 2 760 352 B1 extracted from espacenet.com database on Nov. 13, 2023, 1 page.
(Continued)

*Primary Examiner* — Ashley L Fishback
(74) *Attorney, Agent, or Firm* — Howard & Howard Attorneys PLLC

(57) ABSTRACT

An ultrasonic surgical assembly for use with a surgical handpiece to provide air cooling of an ultrasonic tip. An ultrasonic tip comprises a shaft and a cutting portion. The tip comprises a first side and a second side that are substantially planar and a cutting head. The tip is removably coupled to a horn. The assembly comprises an irrigation sleeve defining a lumen. The sleeve at least partially surrounds the shaft, defines an inlet aperture, and comprises a conduit in fluid communication with the lumen. The conduit has an outlet aperture and is configured for being connected to a liquid source. The tip comprises a sealing member coupled to its outer surface and has a first bore defining an air inlet disposed proximal the sealing member and a second bore
(Continued)

extending from the proximal end of the shaft to the first bore to form a fluid bath therebetween.

19 Claims, 10 Drawing Sheets

(56) References Cited

U.S. PATENT DOCUMENTS

| | | | |
|---|---|---|---|
| 5,695,510 | A | 12/1997 | Hood |
| 5,746,756 | A | 5/1998 | Bromfield et al. |
| 6,159,176 | A | 12/2000 | Broadwin et al. |
| 6,177,755 | B1 | 1/2001 | Hur |
| 6,379,371 | B1 | 4/2002 | Novak et al. |
| 6,443,969 | B1 | 9/2002 | Novak et al. |
| 6,497,715 | B2 | 12/2002 | Satou |
| 6,723,110 | B2 | 4/2004 | Timm et al. |
| 6,799,729 | B1 | 10/2004 | Voic |
| 6,955,680 | B2 | 10/2005 | Satou et al. |
| D551,764 | S | 9/2007 | Easley |
| 7,871,392 | B2 | 1/2011 | Sartor |
| 8,092,475 | B2 | 1/2012 | Cotter et al. |
| 8,109,931 | B2 | 2/2012 | Vercellotti et al. |
| 8,118,823 | B2 | 2/2012 | Cotter et al. |
| 8,142,460 | B2 | 3/2012 | Cotter et al. |
| 8,221,392 | B2 | 7/2012 | Dextradeur et al. |
| 8,343,178 | B2 | 1/2013 | Novak et al. |
| 8,353,912 | B2 | 1/2013 | Darian et al. |
| 8,512,340 | B2 | 8/2013 | Easley et al. |
| 8,758,011 | B2 | 6/2014 | Regere et al. |
| 8,911,460 | B2 | 12/2014 | Neurohr et al. |
| 9,358,017 | B2 | 6/2016 | Rad |
| 9,387,005 | B2 | 7/2016 | Voic |
| 9,421,072 | B2 | 8/2016 | Lesage et al. |
| 9,693,793 | B2 | 7/2017 | Akagane |
| 9,788,852 | B2 | 10/2017 | Voic |
| 9,962,183 | B2 | 5/2018 | Wuchinich |
| D820,441 | S | 6/2018 | Ketelhohn et al. |
| 10,016,208 | B2 | 7/2018 | Gouery et al. |
| 10,178,997 | B2 | 1/2019 | Edwards |
| 10,206,704 | B2 | 2/2019 | Voic et al. |
| 10,391,210 | B2 | 8/2019 | Manandhar et al. |
| 10,588,645 | B1 | 3/2020 | Cao et al. |
| D882,083 | S | 4/2020 | Qun |
| D882,789 | S | 4/2020 | Qun |
| D888,955 | S | 6/2020 | Qun |
| 10,687,840 | B1 | 6/2020 | Cotter et al. |
| 10,799,260 | B2 | 10/2020 | Cotter et al. |
| 10,813,551 | B2 | 10/2020 | Feng et al. |
| 10,864,012 | B2 | 12/2020 | Zhan et al. |
| 10,896,686 | B2 | 1/2021 | Truong et al. |
| 11,065,421 | B2 | 7/2021 | Dextradeur |
| 11,173,327 | B2 | 11/2021 | Cotter et al. |
| D939,089 | S | 12/2021 | Cao et al. |
| 11,191,553 | B2 | 12/2021 | Ketelhohn et al. |
| 11,207,084 | B2 | 12/2021 | Feng et al. |
| D943,745 | S | 2/2022 | Cao et al. |
| D947,124 | S | 3/2022 | Cao et al. |
| D947,379 | S | 3/2022 | Cao et al. |
| 11,284,915 | B2 | 3/2022 | Cotter et al. |
| D950,736 | S | 5/2022 | Cao et al. |
| 11,389,189 | B2 | 7/2022 | Cao et al. |
| 11,490,919 | B2 | 11/2022 | Cao et al. |
| 11,497,518 | B2 | 11/2022 | Scheller et al. |
| 11,583,895 | B2 | 2/2023 | Feng et al. |
| 11,612,682 | B2 | 3/2023 | Manandhar et al. |
| 11,627,980 | B2 | 4/2023 | Cao et al. |
| 11,684,375 | B2 | 6/2023 | Cao et al. |
| 11,738,215 | B2 | 8/2023 | Cotter et al. |
| 11,779,366 | B2 | 10/2023 | Sun et al. |
| 2003/0204199 | A1 | 10/2003 | Novak et al. |
| 2005/0177184 | A1 | 8/2005 | Easley |
| 2008/0208231 | A1 | 8/2008 | Ota et al. |
| 2010/0168741 | A1 | 7/2010 | Sanai et al. |
| 2013/0023866 | A1 | 1/2013 | Stringham et al. |
| 2013/0103066 | A1 | 4/2013 | Rad |
| 2015/0073457 | A1 | 3/2015 | Stoddard et al. |
| 2016/0081699 | A1 | 3/2016 | Edwards |
| 2017/0319226 | A1 | 11/2017 | Voic et al. |
| 2017/0340339 | A1 | 11/2017 | Madan et al. |
| 2017/0348051 | A1 | 12/2017 | Paulus et al. |
| 2019/0159793 | A1 | 5/2019 | Cotter et al. |
| 2020/0093507 | A1 * | 3/2020 | James .................... A61B 90/98 |
| 2020/0107848 | A1 | 4/2020 | Apperson et al. |
| 2020/0205850 | A1 | 7/2020 | Cao et al. |
| 2020/0253631 | A1 | 8/2020 | Apperson et al. |
| 2021/0022763 | A1 | 1/2021 | Cotter et al. |
| 2021/0030435 | A1 | 2/2021 | Cao et al. |
| 2021/0307777 | A1 | 10/2021 | Cao et al. |
| 2021/0307778 | A1 | 10/2021 | Cao et al. |
| 2021/0393286 | A1 | 12/2021 | Gras et al. |
| 2022/0087699 | A1 | 3/2022 | Ketelhohn et al. |
| 2022/0211407 | A1 | 7/2022 | Cotter et al. |

FOREIGN PATENT DOCUMENTS

| | | | | |
|---|---|---|---|---|
| WO | WO-2018022311 | A1 * | 2/2018 | ....... A61B 17/22004 |
| WO | 2020068756 | A1 | 4/2020 | |

OTHER PUBLICATIONS

English language abstract for EP 2 768 403 B1 extracted from espacenet.com database on Nov. 13, 2023, 1 page.
Heavey, Cathal A., "Ultrasonic Cutting of Bone", University College Dublin, Dec. 2013, 256 pages.
Integra Lifesciences, "CUSA Clarity 23 kHz Tips Webpage", https://www.integralife.com/cusa-clarity-23-khz-tips/product/cusa-tissue-ablation-cusa-clarity-system-accessories-cusa-clarity-23-khz-tips, 2017-2023, 2 pages.
Integra Lifesciences, "CUSA Excel Tips Webpage", https://www.integralife.com/cusa-excel-tips/product/cusa-tissue-ablation-cusa-excel-system-accessories-cusa-excel-tips, 2017-2023, 2 pages.
International Search Report for Application No. PCT/IB2021/055077 dated Nov. 26, 2021, 3 pages.
Lifehealthcare, "SonaStar Ultrasonic Aspirator Webpage", https://www.lifehealthcare.com.au/products/sonostar/, 2023, 4 pages.
Partial International Search Report for Application No. PCT/IB2021/055077 dated Nov. 26, 2021, 2 pages.
Soring GMBH, "LEVICS Micro Instrument Webpage", https://www.soering.de/en/products/micro-instruments-for-neurosurgery/levics-micro-instrument-for-neurosurgery/, 2020, 5 pages.

* cited by examiner

ULTRASONIC SURGICAL ASSEMBLY WITH AIR COOLING BROAD KNIFE AND IRRIGATION SLEEVE

RELATED APPLICATIONS

This application is a National Stage Entry of International Patent Application No. PCT/IB2021/055077, filed Jun. 9, 2021, which claims priority to and all the benefits of U.S. Provisional Patent Application No. 63/127,802, filed Dec. 18, 2020, and U.S. Provisional Patent Application No. 63/197,773, filed Jun. 7, 2021, the entire contents of each of which are hereby incorporated by reference.

SUMMARY

An ultrasonic surgical assembly to provide air cooling of an ultrasonic tip is disclosed. The ultrasonic surgical assembly includes an ultrasonic tip and an irrigation sleeve. The ultrasonic tip comprises a shaft and a cutting portion and has a first side and a second side. The first side is substantially planar and extends from a proximal end to a distal end. The second side is substantially planar, is disposed opposite the first side, and extends from the proximal end to the distal end. The cutting portion includes a cutting head, which is disposed at the distal end. The ultrasonic tip is removably coupled to a horn. The shaft further comprises a longitudinal axis. The irrigation sleeve has a distal region and a proximal region and defines a lumen that extends along the longitudinal axis. The irrigation sleeve at least partially surrounds the shaft and defines an inlet aperture. The irrigation sleeve further comprises a first conduit in fluid communication with the lumen. The first conduit has an outlet aperture and is configured for being connected to a liquid source. The ultrasonic tip further comprises a sealing member coupled to its outer surface and further defines a first bore and a second bore. The first bore defines an air inlet disposed proximal to the sealing member, and the second bore extends from the proximal end of the shaft to the first bore to form a fluid path between the first bore and the second bore.

A second ultrasonic surgical assembly is disclosed. The assembly includes an ultrasonic instrument, an ultrasonic tip, and an irrigation sleeve. The ultrasonic instrument comprises a housing, a transducer, and a horn. The housing comprises a proximal portion and a distal portion. The transducer is at least partially disposed within the housing. The horn is coupled to the transducer. The ultrasonic tip comprises a shaft and is removably coupled to the horn. The irrigation sleeve defines a lumen and comprises a body, a sheath, and an irrigation conduit. The body is releasably coupled to the distal portion of the housing and has a distal region and a proximal region. The body defines a helical groove which at least partially surrounds the shaft when the ultrasonic tip is in the lumen of the irrigation sleeve. The sheath is coupled to and disposed over a portion of the body to surround at least a full revolution of the helical groove. The sheath has a proximal end and an opposing distal end. The irrigation conduit is disposed within the helical groove for conveying irrigation fluid and defines an inlet aperture and an outlet aperture. The inlet aperture is disposed at the proximal region of the body, and an outlet aperture is disposed at a distal region of the body. The irrigation fluid enters the irrigation conduit at the inlet aperture and exits the irrigation conduit at the outlet aperture.

An ultrasonic tip is disclosed that comprises a shaft and a cutting portion. The shaft defines a longitudinal axis. The cutting portion defines a first side that is substantially planar and a second side that is substantially planar and includes a cutting head. The cutting portion includes a base portion having a transverse dimension between the first side and the second side that extends perpendicular to a longitudinal axis of the cutting head. The cutting portion further includes a tapered portion that comprises a bevel and that extends from the base portion to a cutting edge. The cutting edge comprises a length and has a U-shaped profile having a first leg portion, a second leg portion, and an arcuate shaped distal portion. The first leg portion and the second leg portion are parallel to one another. Moreover, the largest cross-sectional area of the ultrasonic tip defines a cross-sectional area of a first slice. A cross-sectional area of a second slice is defined at a location 20 mm proximal to a distal end of the ultrasonic tip. The second slice and the first slice are each perpendicular to the longitudinal axis of the shaft. The cross-sectional area of the second slice is 16.7-20% of the cross-sectional area of the first slice.

A second ultrasonic surgical assembly to provide air cooling of an ultrasonic tip is disclosed. The ultrasonic surgical assembly comprises an ultrasonic instrument, an ultrasonic tip, an irrigation sleeve, and a sealing member. The ultrasonic instrument has a proximal region and a distal region and comprises a housing, a transducer, and a horn. The housing comprises a proximal portion and a distal portion. The transducer is at least partially disposed within the housing. The horn is coupled to the transducer, which is configured to be coupled to a suction source by a first coupler. The ultrasonic tip comprises a shaft and a cutting portion and is removably coupled to the horn by a tip coupler. The shaft comprises a longitudinal axis. The irrigation sleeve has a distal region and a proximal region and defines a lumen. The irrigation sleeve at least partially surrounds the shaft and defines an inlet aperture configured to receive irrigation liquid from an irrigation source. The irrigation sleeve further comprises a first conduit in fluid communication with the lumen. The first conduit is configured to convey irrigation liquid from the inlet aperture to an outlet aperture. The sealing member is positioned between an outer surface of the ultrasonic tip and an inner surface of the lumen. The ultrasonic tip defines a first bore and a second bore. The first bore defines an air inlet disposed proximal to the sealing member when the irrigation sleeve and the ultrasonic tip are coupled to the ultrasonic instrument. The second bore extends from a proximal end of the ultrasonic tip to the first bore. The second bore is in communication with the suction source through the tip coupler. The irrigation sleeve defines a third bore proximal the first bore when the irrigation sleeve and the ultrasonic tip are coupled to the ultrasonic instrument. The ultrasonic surgical assembly defines a path to draw air from an ambient environment through the third bore, then through the first bore, and back through the second bore before the air exits the ultrasonic surgical assembly at the first coupler.

A method of cutting bone with an ultrasonic tip is disclosed. The method includes providing an ultrasonic tip, which comprises a shaft and a cutting portion and is removably coupled to a horn by a tip coupler. The horn is coupled to a transducer, and the transducer is coupled to a suction source by a first coupler. The shaft comprises a longitudinal axis. The ultrasonic tip defines a first bore defining an air inlet and a second bore extending from a proximal end of the ultrasonic tip to the first bore. The first bore is transverse to the second bore, and the second bore is in communication with the suction source via the tip coupler. The method further includes providing an irrigation sleeve having a distal region and a proximal region and defining a lumen.

The irrigation sleeve at least partially surrounds the shaft and is configured to be coupled to an irrigation source with an inlet aperture configured to receive irrigation liquid from the irrigation source. The irrigation sleeve defines a first conduit in fluid communication with the lumen. The first conduit is configured to convey irrigation liquid from the inlet aperture to an outlet aperture. The method further includes drawing air via the suction source through the second bore and the first bore to cool the ultrasonic tip.

A third ultrasonic surgical assembly is disclosed. The assembly includes an ultrasonic instrument, an ultrasonic tip, and an irrigation sleeve. The ultrasonic instrument includes a housing, a transducer, and a horn. The housing comprises a proximal portion and a distal portion. The transducer is at least partially disposed within the housing. The horn is coupled to the transducer. The ultrasonic tip comprises a shaft and a cutting portion and is removably coupled to the horn. The irrigation sleeve defines a lumen and comprises a body releasably coupled to the distal portion of the housing and has a distal region and a proximal region. The ultrasonic tip further comprises an annular sealing member and defines a groove, with the annular sealing member disposed around the groove, disposed at the proximal region of the body, and positioned between an outer surface of the ultrasonic tip and an inner surface of the lumen when the sleeve and ultrasonic tip are coupled to the ultrasonic instrument. The annular sealing member is configured to prevent movement of fluid proximally to the annular sealing member.

A fourth ultrasonic surgical assembly is disclosed. The assembly includes an ultrasonic instrument, and an irrigation sleeve. The ultrasonic instrument includes a housing, a transducer, and a horn. The housing comprises a proximal portion and a distal portion. The transducer is at least partially disposed within the housing. The horn is coupled to the transducer. The irrigation sleeve defines a lumen and is configured to be removably coupled to a first ultrasonic tip and a second ultrasonic tip. Each of the first ultrasonic tip and the second ultrasonic tip is configured to be removably coupled to the horn by a tip coupler. Each of the first ultrasonic tip and the second ultrasonic tip comprises a shaft, a cutting portion, and an annular sealing member. The cutting portion of the first ultrasonic tip comprises a cutting geometry that is distinct from a cutting geometry of the cutting portion of the second ultrasonic tip. The first ultrasonic tip defines a first groove positioned at a first distance from the tip coupler of the first ultrasonic tip. The second ultrasonic tip defines a second groove positioned at a second distance from the tip coupler of the second ultrasonic tip. The first distance from the tip coupler of the first ultrasonic tip is not equal to the second distance from the tip coupler of the second ultrasonic tip. Each of the first ultrasonic tip and the second ultrasonic tip includes the annular sealing member disposed around the respective first and second grooves. The irrigation sleeve comprises a body and an irrigation conduit. The body is releasably coupled to the distal portion of the housing. The irrigation conduit is coupled to the body and configured to convey irrigation fluid. The irrigation conduit further defines an inlet aperture disposed at a proximal region of the body, and an outlet aperture disposed at a distal region of the body, wherein irrigation fluid enters the irrigation conduit at the inlet aperture and exits the irrigation conduit at the outlet aperture.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

As medical professionals strive for reducing the size of the incisions and the amount of recovery time required following invasive medical procedures, the size of medical instruments used in various medical procedures have become smaller. Many of the medical instruments utilized in performing the various medical procedures may include the use of a cutting accessory, such as an ultrasonic tip. In performing a cutting, shaving, or shaping operation, the cutting accessory will be exposed to varying amounts of force creating stresses within the cutting accessory.

Many of these cutting accessories may also require the use of irrigation or aspiration (i.e., suction) to reduce heat and/or remove debris at the surgical site. One example of a surgical instrument that may utilize irrigation and/or aspiration systems is an ultrasonic surgical handpiece. Generally, one or more lines may be coupled to the ultrasonic surgical handpiece to supply irrigation and/or suction. The ultrasonic surgical handpiece may further comprise a sleeve comprising one or more lumens that may be utilized to direct fluid from an irrigation source toward the surgical site and/or the cutting accessory, i.e., the ultrasonic tip. One such ultrasonic surgical handpiece is described in PCT/US19/52609, entitled "Ultrasonic Surgical Handpiece Assembly", which is hereby incorporated by reference in its entirety.

However, a cutting accessory that is particularly flat or narrow frequently may not include a lumen throughout the entire length of the cutting accessory, i.e., to the cutting edge or blade. Moreover, a higher current within the cutting accessory due to the lack of an aspiration or cooling lumen throughout may cause over-heating of the handpiece. The excessive heat build-up may adversely affects the life span of the handpiece and may also be felt by the surgeon.

Additionally, the shape and geometry of the cutting accessory may affect the amplification factor, or gain, associated with the ultrasonic instrument. By configuring the ultrasonic tip with lower gain in certain implementations, the inventors realized that various benefits may be achieved, including a reduction in stalling, drawing less power to drive the tip, and the ability to drive the tip at a higher current to the ultrasonic handpiece, which may improve cutting rate without an increase in stalling.

Figure 1:
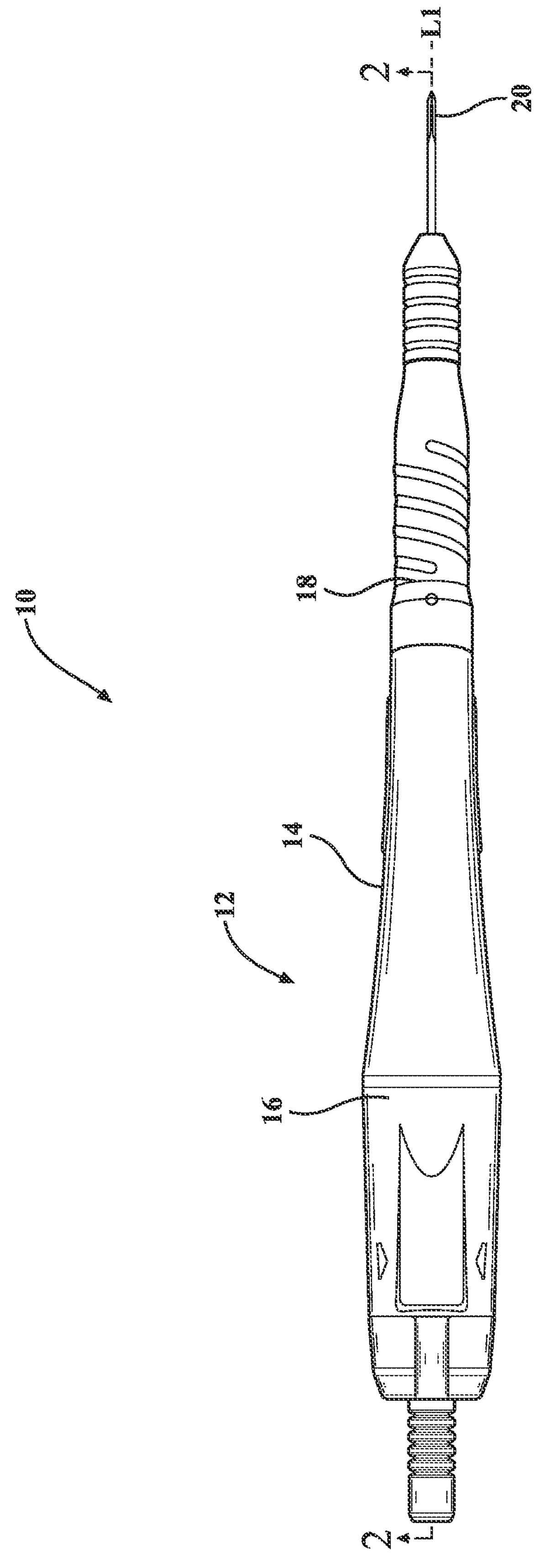
FIG. 1 is a top view of an ultrasonic surgical handpiece assembly.
Figure 2:
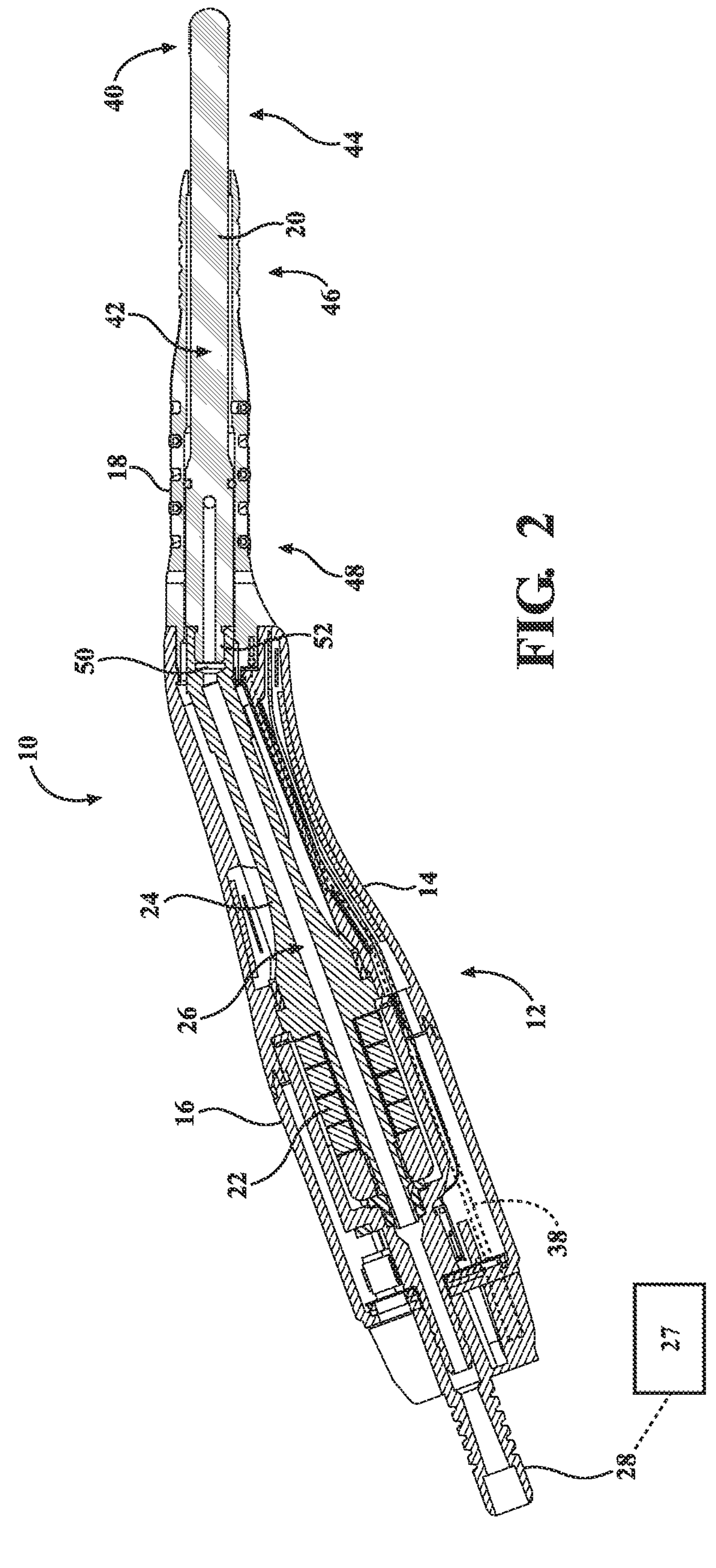
FIG. 2 is a sectional view of the ultrasonic surgical handpiece assembly of FIG. 1.

FIGS. 1 and 2 illustrate an exemplary configuration of an ultrasonic surgical handpiece assembly 10 that may be utilized by a medical professional to remove biological material from a patient. The ultrasonic surgical handpiece assembly 10 may comprise an ultrasonic handpiece 12 including a distal housing portion 14 and a proximal housing portion 16. An irrigation sleeve 18 may be removably coupled to the distal housing portion 14 of the ultrasonic surgical handpiece 12. The irrigation sleeve 18 and an ultrasonic tip 20 may be configured such that the irrigation sleeve 18 surrounds at least a portion of the ultrasonic tip 20 along a length of the ultrasonic tip 20 when both the irrigation sleeve 18 and the ultrasonic tip 20 are coupled to the ultrasonic handpiece 12. The irrigation sleeve 18 and the ultrasonic tip 20 may at least in part comprise an ultrasonic sleeve assembly 14.

FIG. 2 illustrates a sectional view of the ultrasonic surgical handpiece assembly 10 of FIG. 1. As illustrated in FIG. 2, the ultrasonic handpiece 12 may comprise a transducer 22 disposed within a void defined by the distal housing portion 14 and the proximal housing portion 16 of the ultrasonic handpiece 12. The transducer 22 may comprise a plurality of piezoelectric elements or magnetostrictive elements configured to generate mechanical energy.

The ultrasonic handpiece 12 may also comprise a horn 24 that may be at least partially disposed within the void defined by the distal housing portion 14 and the proximal housing portion 16 of the ultrasonic handpiece 12. The horn 24 may comprise a distal end and a proximal end. The proximal end of the horn 24 may be coupled to a distal end of the transducer 22. The transducer 22 may be configured to provide the mechanical energy generated by the piezoelectric element or magnetostrictive element to the horn 24. The horn 24 may also be configured to define a horn lumen 26 that extends from the distal end to the proximal end of the horn 24. The horn lumen 26 may define a portion of a passageway that extends through the ultrasonic handpiece 12 to provide aspiration. The horn lumen 26 has a distal end and a proximal end, and the proximal end may be in communication with a suction source 27). The transducer 22 may be coupled to the suction source 27 via a coupler 28.

The ultrasonic handpiece 12 may further comprise an irrigation line 38 that is disposed within the void defined by the distal housing portion 14 and the proximal housing portion 16 of the ultrasonic handpiece 12. The irrigation line 38 may be configured to extend from the proximal end to the distal end of the ultrasonic handpiece 12. The irrigation line 38 may serve to channel a liquid, such as water or saline from an irrigation system that is coupled to the ultrasonic handpiece 12 through the irrigation sleeve 18. It should be appreciated that the irrigation line 38 may route directly from an irrigation source (not shown) to the irrigation sleeve 18 (i.e., the irrigation line 38 need not be always routed through the handpiece 12).

The ultrasonic tip 20 may comprise a shaft 42 that includes a distal region 44, an intermediate region 46, and a proximal region 48, all disposed along a longitudinal axis L1. The ultrasonic tip 20 may also comprise a coupling feature 50 positioned at the proximal region 48 of the shaft 42 and is configured to couple the proximal region 48 of the ultrasonic tip 20 to the distal end of the horn 24 to allow the horn 24 to be in mechanical communication with the ultrasonic tip 20. The coupling feature 50 may be a threaded coupler 52 configured to engage a corresponding threaded coupler on the distal end of the horn 24. The ultrasonic tip 20 may be threaded into the horn 24 and tightened to a predetermined torque specification to removably secure the ultrasonic tip 20 to the ultrasonic handpiece 12. While not illustrated in the figures, it is contemplated that the coupling feature 50 may be configured as a quick connection, quarter turn fitting, or similar coupling mechanism. It is further contemplated that the coupling feature 50 may be configured to permanently affix the ultrasonic tip 20 to the handpiece 12. For example, the ultrasonic tip 20 may be coupled to the ultrasonic handpiece 12 by a weld, epoxy, or similar coupling method.

Alternatively, it is also contemplated that the ultrasonic tip 20 and the horn 24 may be formed as a unitary component. In such a configuration, the ultrasonic tip 20 may include a base (horn) 24 for coupling to the transducer 22, and a body comprised of the shaft 42 and a cutting portion 40. The body 40, 42 extends from and is coupled to the base 24 at the shaft 42. The body 40, 42 extends from the shaft 42 to the cutting portion 40 along the longitudinal axis L1.

In some aspects, such as the illustrated aspect, the shaft 42 is free of a lumen in the distal region 44. Said differently, the ultrasonic tip may be free of a lumen in the portions of the cutting tip that feature a rectangular shaped cross-sectional area. The shaft 42 may be made of a metal material such as titanium alloy, stainless steel, etc. or a non-metallic material such as a composite, depending on the application. In one aspect, the shaft 42 and the cutting portion 40 may be integral, unitary, and one-piece. In another aspect, the cutting portion 40 of the ultrasonic tip 20 may be attached to the shaft 42 by a suitable mechanism such as threads (not shown).

Figure 3:
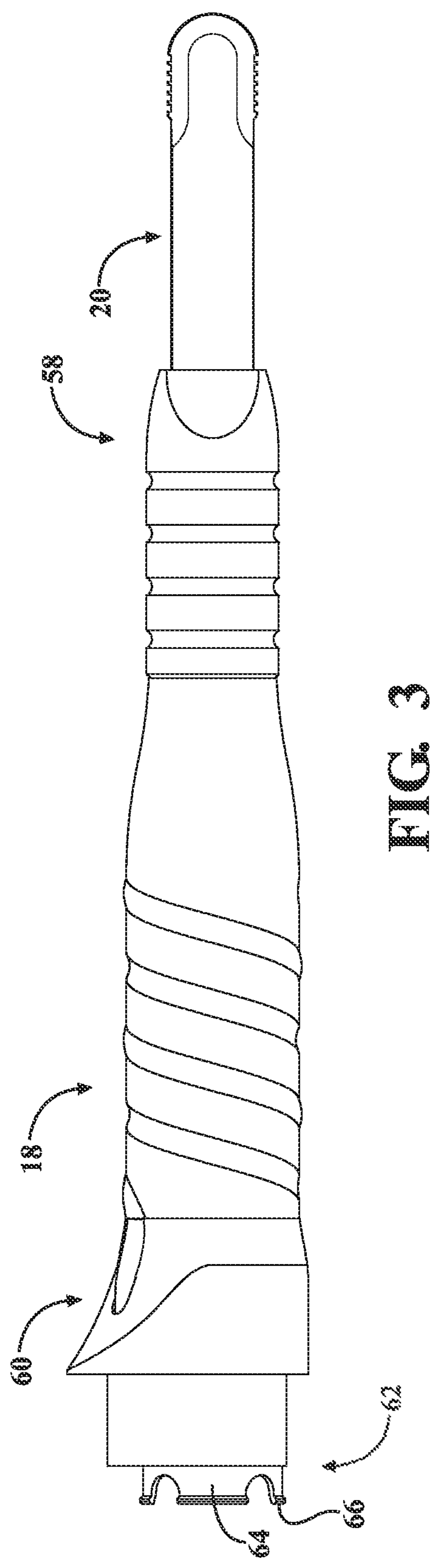
FIG. 3 is a top view of an ultrasonic tip and an irrigation sleeve with the ultrasonic tip positioned within the irrigation sleeve.

FIG. 3 illustrates a top view of an exemplary configuration of the irrigation sleeve 18 having a distal region 58 and a proximal region 60. The irrigation sleeve 18 may comprise an irrigation sleeve coupling mechanism 62 on the proximal region 60 of the irrigation sleeve 18. The irrigation sleeve coupling mechanism 62 may comprise one or more fingers 64 extending proximally from the proximal region 60 of the irrigation sleeve 18. Each of the one or more fingers 64 may comprise a tab 66 extending in a radially outward direction relative to a longitudinal axis L1 of the irrigation sleeve 18. The fingers 64 act as the male fitting configured to couple with a female fitting (not shown) on the ultrasonic handpiece 12 to create a snap-fit or interference fit. It is contemplated that other types of irrigation sleeve coupling mechanisms 62 may be used to couple the irrigation sleeve 18 to the ultrasonic handpiece 12. By way of example and not limitation, the irrigation sleeve coupling mechanisms 62 may be configured as a threaded connection. It should be appreciated that the irrigation sleeve 18 described herein may be used in conjunction with other tip designs than illustrated here.

Figure 4A:
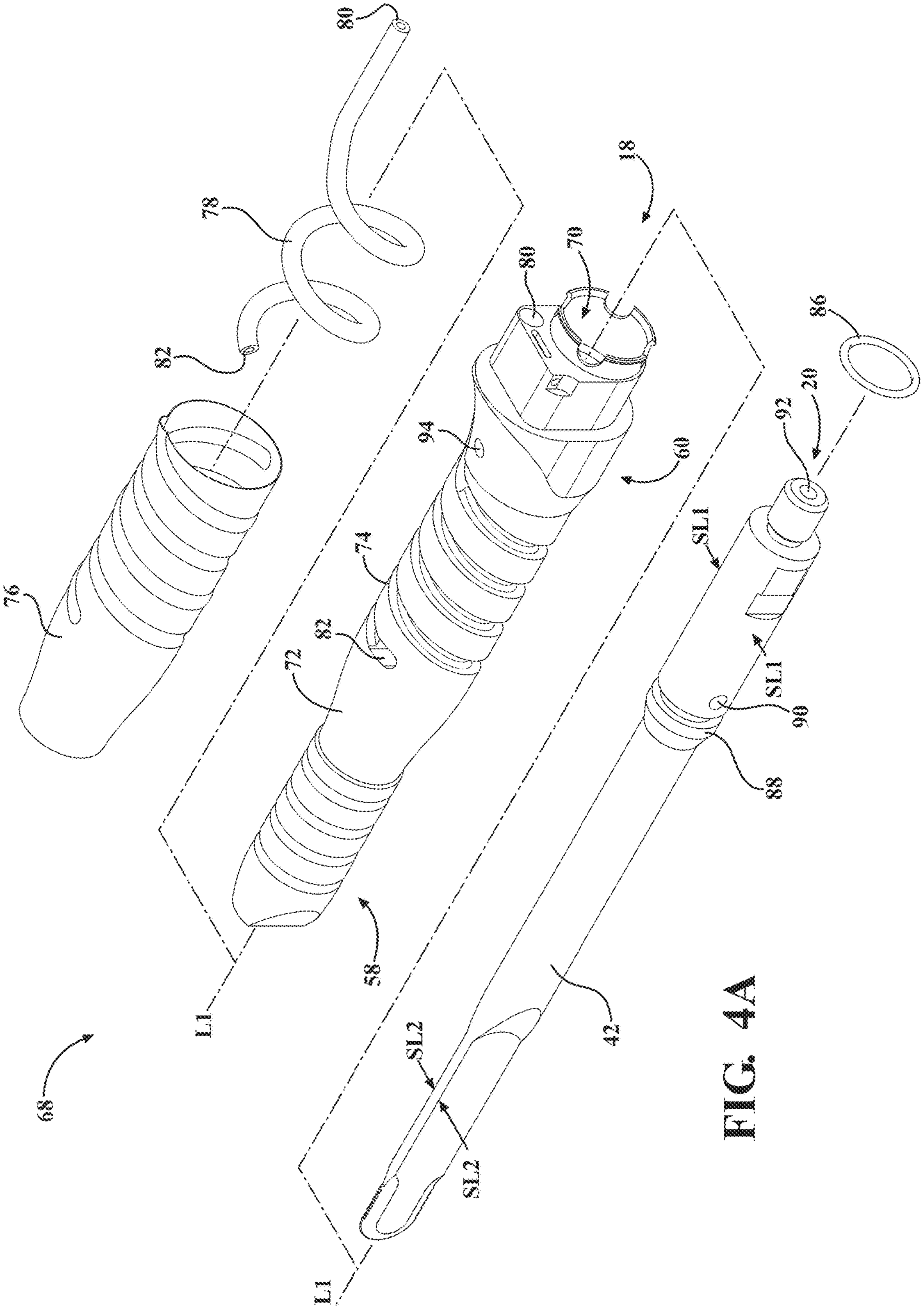
FIG. 4A is an exploded view of an ultrasonic tip and irrigation sleeve assembly.

Referring now to FIG. 4A, an exploded view an ultrasonic tip and irrigation sleeve assembly 68 is illustrated. The irrigation sleeve assembly 68 includes the irrigation sleeve 18 which defines a lumen 70 extending along the longitudinal axis L1. The irrigation sleeve 18 may have a sleeve body 72 defining a helical groove 74. In an assembled configuration, and when the ultrasonic tip 20 is inserted through the irrigation sleeve 18, the irrigation sleeve 18 may at least partially surround the shaft 42 of the ultrasonic tip 20 when the ultrasonic tip 20 is disposed within the lumen 70 of the irrigation sleeve 18 and the irrigation sleeve 18 is coupled to the handpiece.

The irrigation sleeve assembly 68 may further comprise a sheath 76 having a proximal end and a distal end to correspond with the proximal region 60 and distal region 58 of irrigation sleeve 18, respectively. The sheath 76 may be coupled to and disposed over at least a portion of the sleeve body 72 to surround at least a full revolution of the helical groove 74, but can optionally surround more than two or three revolutions of the helical groove to provide sufficient retention.

The location of helical groove 74 may be different on different tips. By way of example and not limitation, in some configurations, one ultrasonic tip may define a groove positioned at a first distance from a tip coupler (e.g., coupling feature 50) of said tip, whereas a different ultrasonic tip may define a groove positioned at a second distance from a tip coupler (e.g., coupling feature 50) of said tip. In some configurations, the first distance is different from the second distance. This may be useful because different tips may have different node and anti-node locations. It may be useful to position the sealing member align with the node or anti-node of the particular tip.

Figure 5:
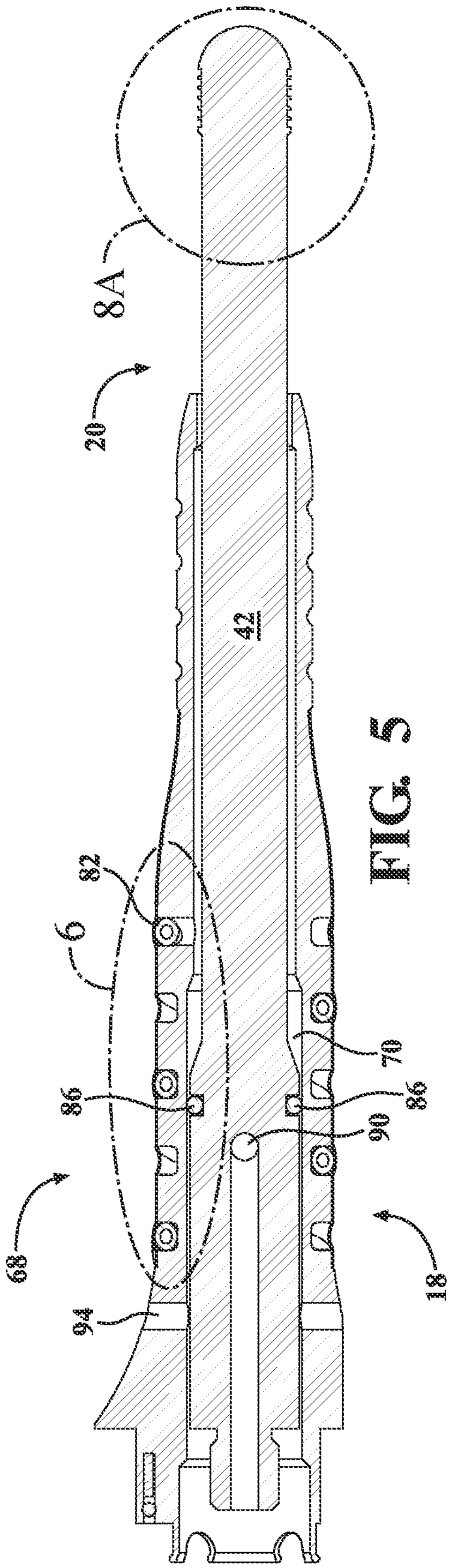
FIG. 5 is sectional view of the irrigation sleeve assembly of FIG. 3 in an assembled configuration with the tip inserted therethrough.

Referring to FIG. 5, a sectional view of the irrigation sleeve assembly 68 of FIG. 3 in an assembled configuration with the tip inserted therethrough is illustrated. The assembled irrigation sleeve assembly 68 with the ultrasonic tip 20 inserted therethrough shows the ultrasonic tip 20 disposed within the lumen 70 such that the irrigation sleeve 18 partially surrounds the shaft 42.

Figure 6:
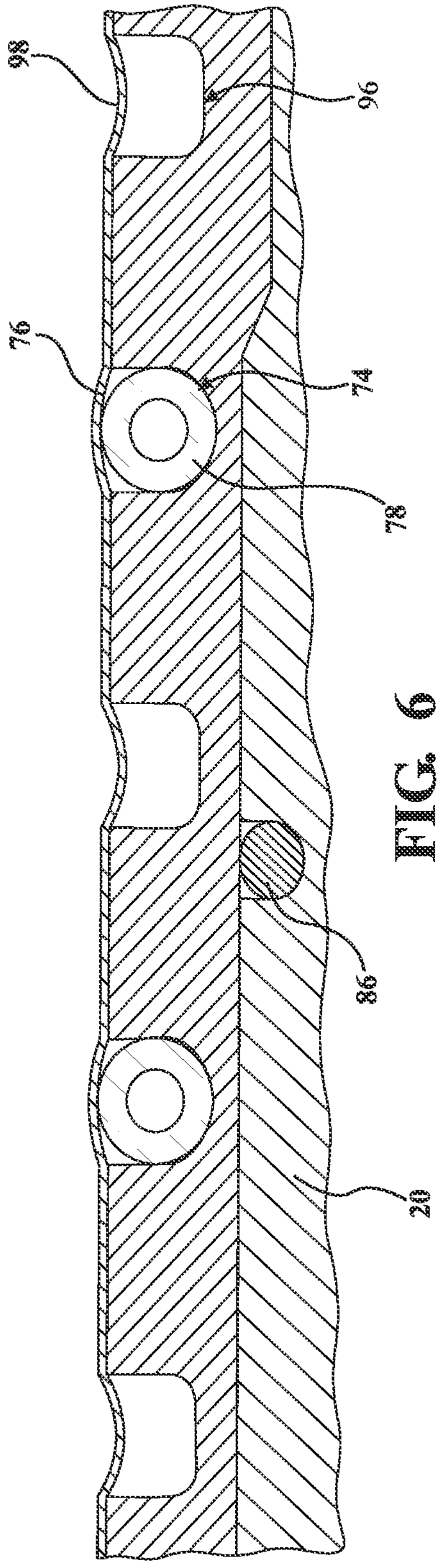
FIG. 6 is a partial sectional view of the ultrasonic tip, irrigation sleeve, sheath, and irrigation conduit of the irrigation sleeve assembly of FIG. 5.

Referring now to FIG. 6, a partial sectional view of ultrasonic tip 20, the irrigation sleeve 18, sheath 76, and an irrigation conduit 78 of the irrigation sleeve assembly of FIG. 5 is illustrated. The sheath 76 is disposed at least partially over irrigation sleeve 18 to surround at least a full revolution of the helical groove 74, covering the irrigation conduit 78.

In some configurations, the sleeve body 72 may define a second helical groove 96. The second helical groove 96 may be free of the irrigation conduit 78, and may also be partially surrounded by the sheath 76, in other words, one or more revolutions of the second helical groove 96 may be surrounded by the sheath 76.

The sheath 76 may be comprised of a heat-shrink or other suitable material that allows it to deform to the shape of the irrigation conduit 78, as well as the underlying contours of the sleeve body 72, which may include the second helical groove 96. When the sheath 76 is contoured to the second helical groove 96, it may define undulations 98 useful for gripping by a user.

Referring again to FIG. 4A, the irrigation sleeve assembly 68 may further comprise the irrigation conduit 78 disposed within the helical groove 74 for conveying irrigation fluid. The irrigation conduit 78 may be in fluid communication with or adjacent to the lumen 70 and may be connected to a liquid source (not shown). The irrigation conduit 78 may define an inlet aperture 80 (disposed at the proximal region 60 of the sleeve body 72 when the irrigation sleeve assembly 68 is in an assembled configuration), and an outlet aperture 82 (disposed at a distal region 58 of the sleeve body 72 when the irrigation sleeve assembly 68 is in an assembled configuration). The irrigation fluid may enter the irrigation conduit 78 at the inlet aperture 80 and exit the irrigation conduit 78 at the outlet aperture 82. In some configurations, the irrigation conduit 78 may comprise a single member defining a continuous length between the inlet aperture 80 and the outlet aperture 82. The irrigation conduit 78 may comprise a flexible material such that the irrigation conduit 78 may be configured to couple directly to a corresponding port of the surgical handpiece 12. In other words, the irrigation conduit 78 may be formed of a material that can be deformed such that the inlet aperture 80 can partially engulf the corresponding port of the ultrasonic handpiece 12 to form the connection to the irrigation source. The helical shape of the groove 74 ensures that the irrigation conduit 78 similarly has a helical shape. This helical shape of the irrigation conduit 78 (tube) and groove 74 provide for a longer fluid return path than a straight return path. This longer path makes it more difficult for fluid to move backward in a proximal direction after it has been initially conveyed through the irrigation conduit 78.

After the fluid has been conveyed through the irrigation conduit 78 distally along the sleeve body 72, the fluid may exit the irrigation conduit 78 at the outlet aperture 82. From there, the fluid may spread to the surface of the sleeve body 72 and/or the shaft 42. In some circumstances, the fluid may return to the aperture 83 and backflow through the irrigation conduit 78. Otherwise, the fluid may return proximally along the sleeve body 72 in a path that flows between an outer diameter of the irrigation conduit 78 and an inner surface of the sleeve body 72 within the sheath 76.

One of the irrigation sleeve 18 and the ultrasonic tip 20 may include a sealing member 86. The sealing member 86 may be an annular sealing member, including, by way of example and not limitation, an O-ring. In some configurations, the sealing member 86 may be coupled to the tip 20. In such an implementation, the sealing member 86 is positioned around a groove 88 defined in an outer surface of the tip 20. This may provide for the sealing member 86 being positioned between the outer surface of the ultrasonic tip 20 and an inner surface of the lumen 70, which may prevent movement of fluid proximal to the sealing member 86 from the outlet aperture 82. Alternatively, the sealing member 86 may be coupled to the sleeve 18, and be positioned to engage the outer surface of the tip 20, again to prevent movement of fluid proximal to the sealing member 86 from the outlet aperture 82.

The sealing member 86 may be also used to dampen the amplitude of vibration of the ultrasonic tip 20. The amplitude of vibration at any point along the ultrasonic tip 20 may depend upon the location along the ultrasonic tip 20 at which vibration is measured. The point along a standing wave where the wave has minimum amplitude is generally referred to as a node. At a node, the vibratory motion is typically minimal. Because the sealing member 86 may be coupled directly to the tip 20, it may be situated anywhere on the ultrasonic tip 20 to decrease transverse motion of the tip 20. In some configurations, it may be suitable to situate the sealing member 86 at or near a node on the tip 20. The location of a node may be different on different ultrasonic tips.

Moreover, because the sealing member 86 may be coupled directly to the tip 20, any sharp surfaces of the ultrasonic tip 20 will never contact the sealing member 86 during placement of the sleeve assembly over the ultrasonic tip 20. Thus, the sealing member 86 is protected from abrasion and other damage when the ultrasonic tip 20 is placed over the sleeve 18. Placement of the sealing member 86 on the ultrasonic tip 20 rather than the irrigation sleeve 18 also prevents the sealing member 86 from spontaneously sliding off or out of the irrigation sleeve assembly 68.

Figure 7:
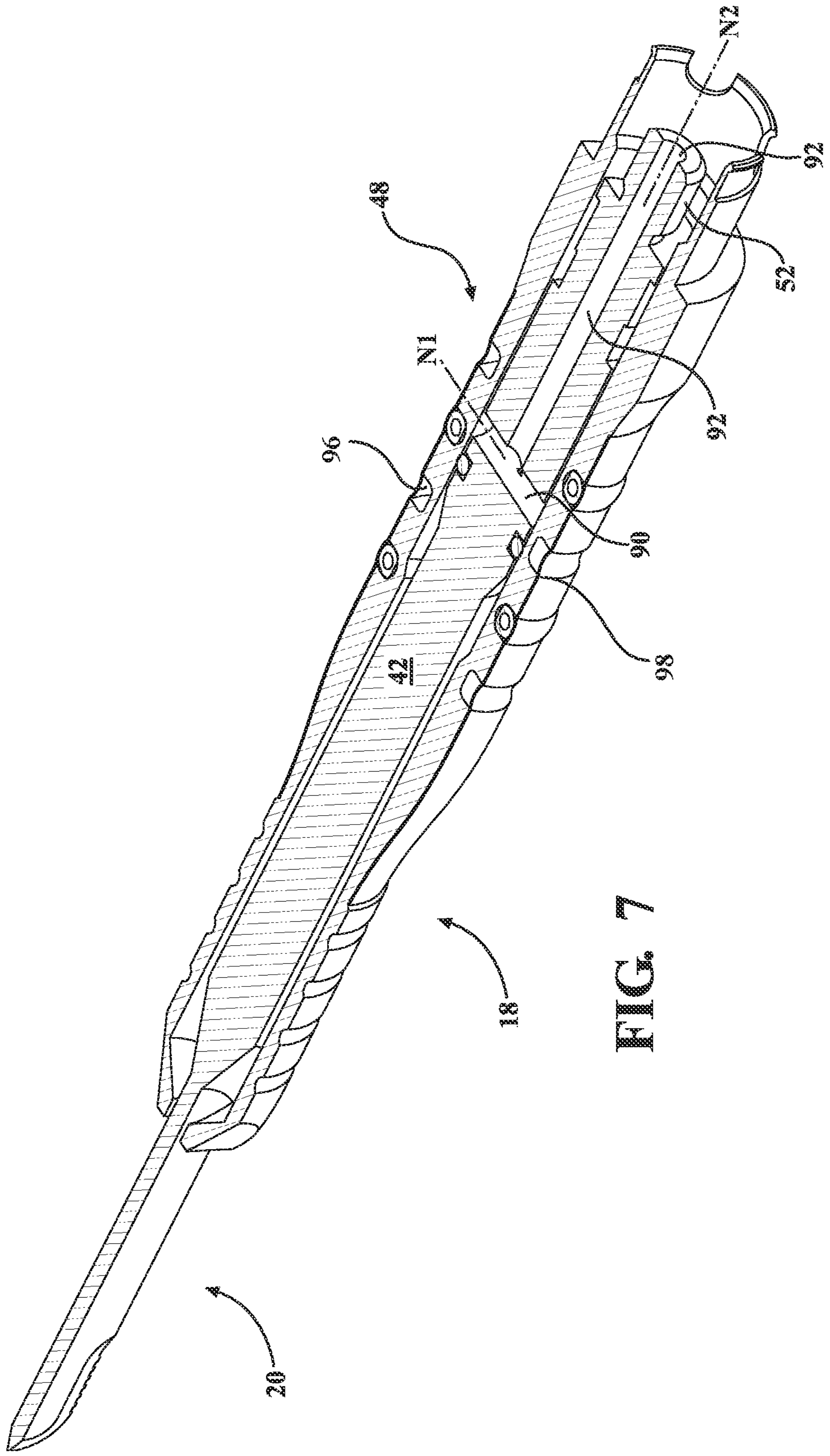
FIG. 7 is an alternate sectional view of the irrigation sleeve assembly with the tip inserted therethrough of FIG. 3 in an assembled configuration.

Referring now to FIG. 7, an alternate sectional view of the irrigation sleeve assembly with the tip inserted therethrough of FIG. 3 in an assembled configuration is illustrated. The ultrasonic tip 20 may define a first bore 90 that behaves as an air inlet. This first bore 90 may be disposed proximal to the sealing member 86 when the irrigation sleeve assembly 68 including the ultrasonic tip 20 are coupled to the handpiece 12. In some configurations, the first bore 90 is located distal the sealing member 86. A second bore 92 may extend from the proximal region 48 of the shaft 42 from the threaded coupler 52 to the first bore 90. In other words, the first bore 90 and the second bore 92 are positioned to be in fluid communication with one another with the first bore 90 transverse the longitudinal axis L1 of the ultrasonic tip 20 and the second bore 92 is concentric with the longitudinal axis L1 of the tip 20. In one example, the axis N1 of the first bore 90 may be perpendicular to an axis N2 of the second bore 92. In some configurations, the first bore 90 may comprise a single bore. In other configurations, such as the configuration illustrated in FIG. 7, the first bore 90 may extend laterally from one side of the ultrasonic tip 20 to the other to form a first bore 90 in each side of ultrasonic tip 20. However, in other configurations, more than one first bore 90 may be included in ultrasonic tip 20, wherein each of more than one first bore 90 is separate from one another (but each may still in communication with second bore 92), rather than forming a single channel with a first bore 90 at each end as shown in FIG. 7. Furthermore, the first bore 90 need not extend all the way through the tip 20, so long as the first bore 90 extends from the outermost periphery to the second bore 92. If there are a plurality of paths defined from the outer periphery of the ultrasonic tip 20 to the second bore 92, those bores may be arranged in a variety of ways, such as being circumferentially arranged about the surface of the tip 20.

In some configurations, the irrigation sleeve assembly 68 further comprises a third bore 94 proximal the first bore 90 when the irrigation sleeve assembly 68 including the ultrasonic tip 20 are coupled to the handpiece. More particularly, the sleeve body 72 may define third bore 94 to further facilitate air ingress from the ambient environment to the first bore 90. Of course, it is contemplated that the irrigation sleeve assembly 68 may include more than one third bore 94 that defines an aperture to allow ambient air to move from outside the irrigation sleeve assembly 68 to the first bore 90 when the suction source 27 is coupled to the tip 20.

In the illustrated configurations, the inlet aperture 80, the outlet aperture 82, the first bore 90, the second bore 92, and the third bore 94 all have circular cross-sectional shapes. However, in some configurations, all or any combinations of the inlet aperture 80, the outlet aperture 82, the first bore 90, the second bore 92, and/or the third bore 94 may have a shape other than a circular shape, such as various polygonal shapes or elliptical shapes.

The irrigation sleeve 18 may be made from any polymer, for example, a thermoplastic. The distal region 58 of the irrigation sleeve 18 may have a portion of frangible sections that could be cut or snipped to change the length of the irrigation sleeve 18.

Referring again to FIG. 5, when the irrigation sleeve assembly 68 is coupled to an irrigation source by a coupler, such as irrigation line 38, it may draw irrigation liquid through the irrigation source via the inlet aperture 80. The irrigation conduit 78 may then convey the irrigation liquid through the inlet aperture 80 to the outlet aperture 82. The conveyance of irrigation liquid through the irrigation sleeve assembly 68 helps provide cooling to the shaft 42 of the ultrasonic tip 20. Additionally, it may help prevent the irrigation sleeve 18 from becoming deformed or melting from excessive heat generated by the motion of the ultrasonic cutting.

In addition, when the irrigation sleeve assembly 68 including the ultrasonic tip 20 are coupled to the handpiece 12, the ultrasonic tip 20 draws air through the third bore 94, then through the first bore 90, back through the second bore 92, and ultimately out through the coupler 28. This movement of air aids in cooling the tip in the area near the sealing member 86, which is prone to overheating due to frictional heat generated by the relative motion between the sealing member 86 and the irrigation sleeve assembly 68.

In addition, the air suction through the tip and/or the sleeve may operates as a smoke evacuation device in some applications. In the illustrated configuration, the ultrasonic tip 20 may be used for lumbar procedures and other relatively "heavy duty" bone-cutting procedures that produce larger amounts of smoke, dust particles, and airborne debris compared to other procedures. The air suction feature may pull some of this from the ambient air surrounding the ultrasonic handpiece 12 and evacuate it through the handpiece 12. The instrument may be used in conjunction with a smoke filter to remove these particulates from the ambient air once aspirated through the tip 20.

Figure 8A:
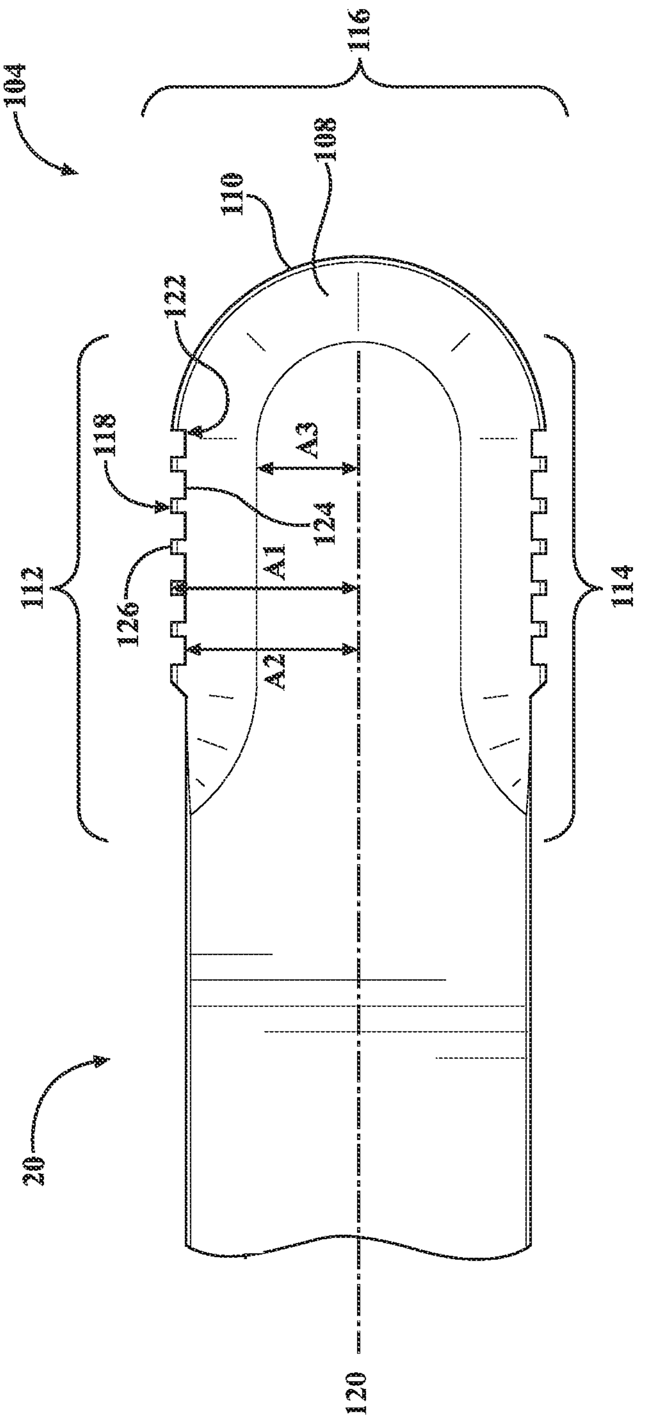
FIG. 8A is a top view of a distal portion of the ultrasonic tip including a cutting head.
Figure 8B:
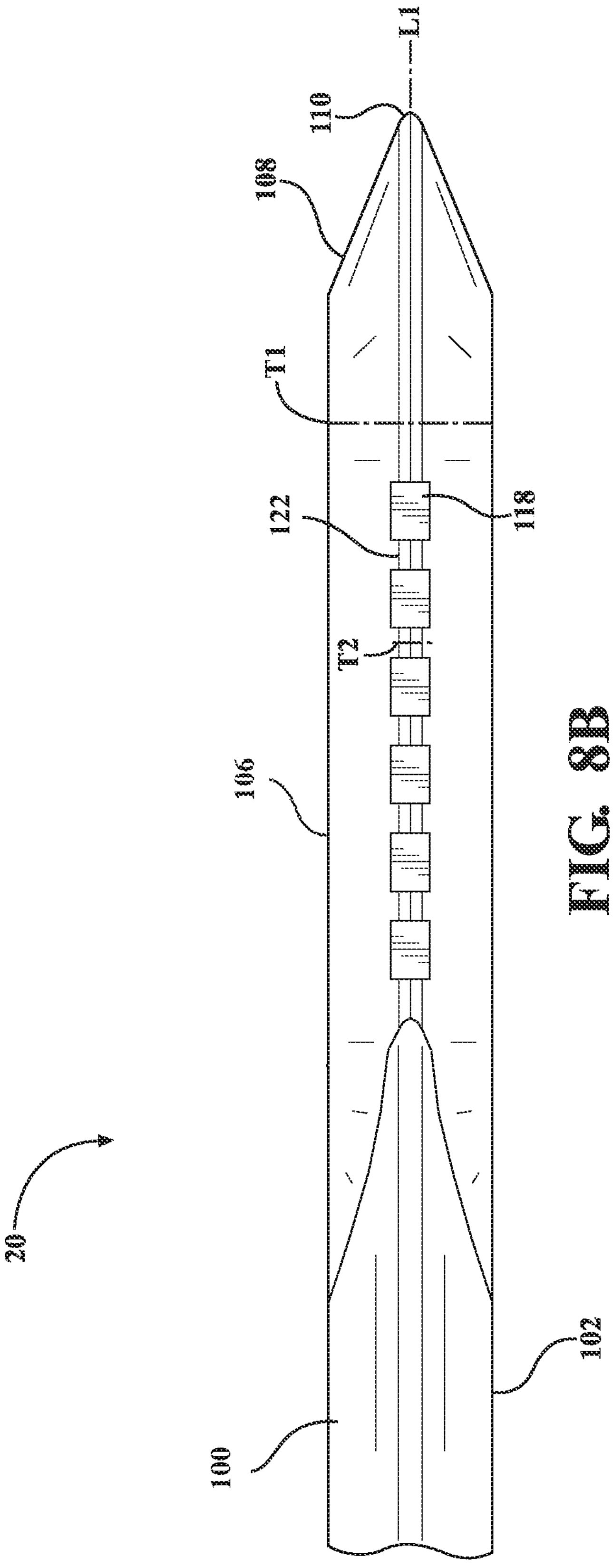
FIG. 8B is a side view a distal portion of the ultrasonic tip including a cutting head.

Referring now to FIGS. 8A-8B, a top view and a side view of a distal portion of the ultrasonic tip including a cutting head are illustrated. The ultrasonic tip 20 may comprise a first side 100 that is substantially planar. The ultrasonic tip 20 may further comprise a second side 102 that is substantially planar that is disposed opposite the first side 100. The ultrasonic tip 20 may further comprise a cutting head (also referred to herein as a "cutting portion") 104 disposed distal the shaft 42. The cutting head 104 may comprise a base portion 106 having a transverse dimension T1 between the first side 100 and the second side 102. The transverse dimension T1 may extend perpendicular to the longitudinal axis L1 of the cutting head 104. The cutting head 104 may further comprise a tapered portion 108 comprising a bevel that extends from the base portion 106 to a cutting edge 110. By way of example and not limitation, in a preferred configuration, the base portion 106 has a transverse dimension of at least 7.975 millimeters. It should be appreciate that other ultrasonic tips may be used with the irrigation sleeve assembly shown above, such as those without the cutting head features described in this application, such as those shown in U.S. Pat. Nos. 6,723,110, 6,497,715, D551764, and 6,955,680, which are all hereby incorporated by reference in their entirety. Similarly, it should be appreciated that the ultrasonic tip may be used with other irrigation sleeve assemblies, such as those shown in PCT/US2019/052609, which is hereby incorporated by reference in its entirety.

The cutting edge 110 comprises a length and may have a U-shaped profile having a first leg portion 112, a second leg portion 114, and an arcuate shaped distal portion 116. By way of example and not limitation, in a preferred configuration, the arcuate shaped distal portion 116 has a thickness of at least 1.35 millimeters. The first leg portion 112 and the second leg portion 114 may be parallel to one another and may each comprise a plurality of cutting teeth, one of which is labeled 118. In some configurations, no more than one half of the length of the cutting edge 110 may have cutting teeth 118. In other configurations, more than one half of the length of the cutting edge 110 may have cutting teeth 118. In some configurations, the arcuate shaped distal portion 116 is free from cutting teeth 118, as is shown in the illustrated configuration in FIGS. 8A-8B.

The cutting portion 40 defines a centerline 120 along the longitudinal axis L1. Moreover, the plurality of cutting teeth 118 comprise at least two adjacent cutting teeth 118 and a notch 122 between each of the adjacent cutting teeth 118. The notch 122 has a transverse dimension T2 along a notch base 124. Each of the cutting teeth 118 has a tooth cutting edge 126. In some configurations, the transverse dimension T2 of the notch 122 is at least 25 times less than the transverse dimension T1 of the base portion 106.

The centerline 120 to the tooth cutting edge 126 defines a first distance A1. The centerline 120 to the notch base 124 defines a second distance A2. The centerline 120 to a starting point of the tapered portion 108 defines a third distance A3. In some configurations, the difference between the first distance A1 and the second distance A2 is less than or equal to 0.25 mm. In some configurations, the first distance A1 is greater than 1.5 times the third distance A3 but is less than 2 times the third distance A3. In the illustrated example, and not by way of limitation, the first distance A1 is 3.4 mm, the second distance A2 is 3.15 mm, and the third distance A3 is 1.85 mm. In this example, the difference between the first distance A1 and the second distance A2 is exactly 0.25 mm. Also, in this example, the first distance A1 is approximately 1.837 times greater than the third distance A3.

The ultrasonic tip 20 may be useful in cutting through both hard and soft tissues. The tooth cutting edges 126 allow for cutting through hard tissue, such as cortical bone. The serrated tooth cutting edges 126 may perform a saw-like operation to cut through denser tissue. By contrast, the cutting edge 110 is a smooth, continuous blade. However, although it may be sharp enough to cut through hard tissue, it may be blunt enough to be atraumatic relative to contacted soft tissue. By way of example and not limitation, the thickness of the cutting edge 110 may be 0.2 mm+/−0.05 mm. As such, the cutting edge 110 can contact soft tissue with minimal risk of puncturing critical structures, such as the spinal cord. The surgeon will feel a tactile change when the cutting edge 110 moves between hard tissue and soft tissue due to the natural differences in the densities between the different tissue structures, indicating the need to terminate cutting when the cutting edge 110 has reached soft tissue. Thus, the ultrasonic tip 20 offers an advantage over the conventional, sharp bone-cutting blades because it is capable of cutting through hard bone structures with both its teeth edges 126 and the cutting edge 110, while avoiding trauma to underlying soft tissues.

Referring again to FIGS. 4A-C, different points along the shaft 42 have varying cross-sectional areas. Although transducers and ultrasonic tips are typically designed to have the same resonance frequency in longitudinal resonance devices, a decrease in the cross-sectional area along the length of the ultrasonic tip can amplify the vibrational velocity of the transducer output face. The amplification factor, otherwise known as gain, is determined by the reduction in cross-sectional area, as well as the shape of the ultrasonic tip. Gain can be measured by dividing the tip displacement by the handpiece displacement.

Figure 4B:
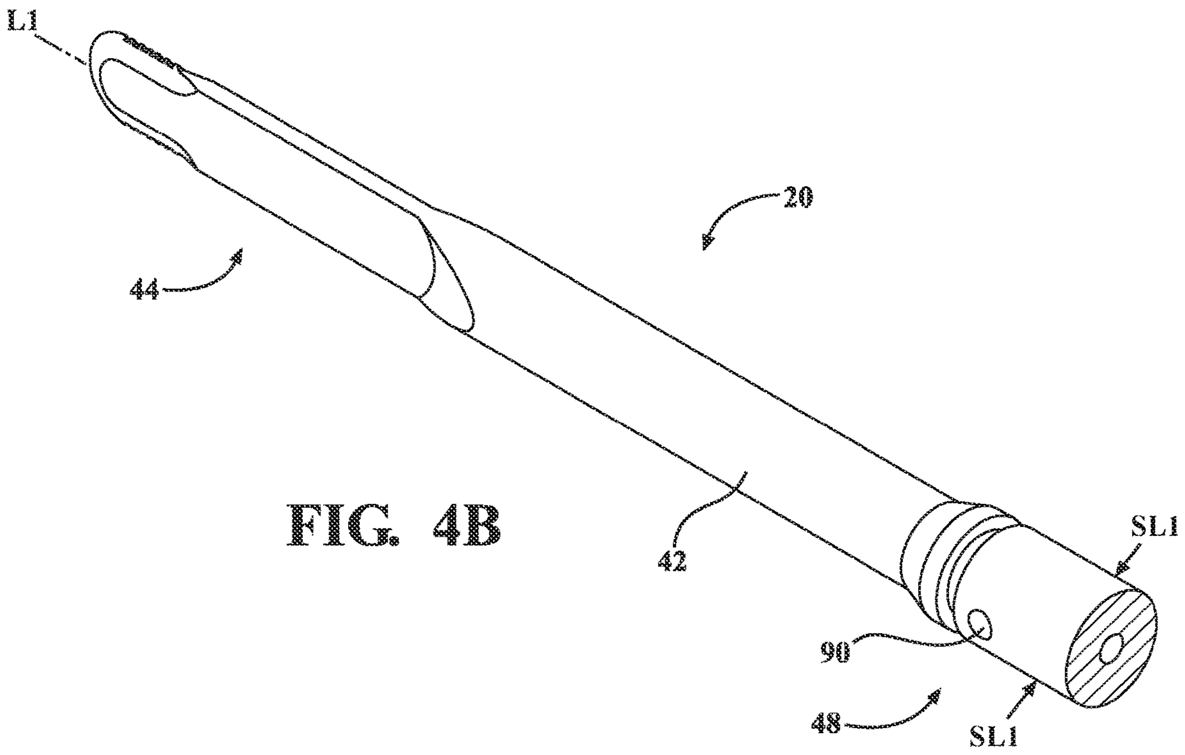
FIG. 4B is a sectional view of the ultrasonic tip of FIG. 4A at a first cross-sectional area.
Figure 4C:
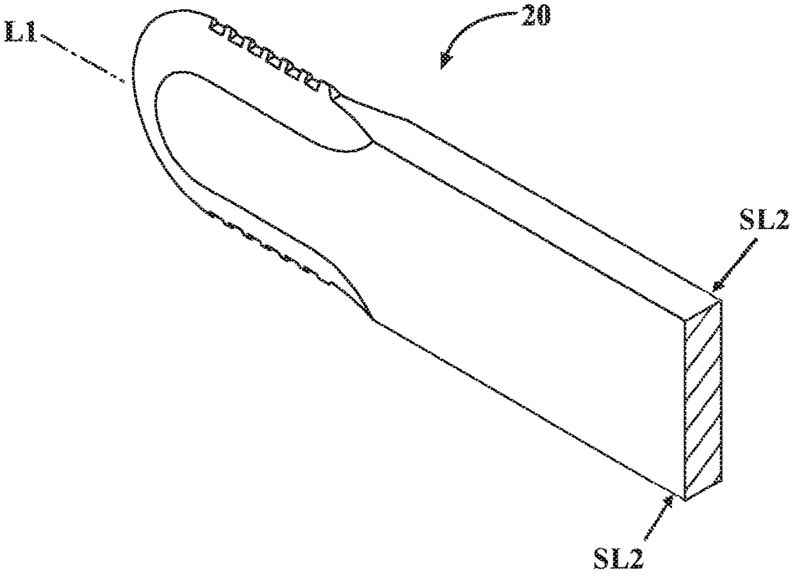
FIG. 4C is a sectional view of the ultrasonic tip of FIG. 4A at a second cross-sectional area.

In the illustrated configuration, a cross-sectional area of a first slice SL1 is defined as the largest circular cross-sectional area of the ultrasonic tip 20 and which defines a plane perpendicular to the longitudinal axis L1. FIG. 4B illustrates a sectional view of the ultrasonic tip of FIG. 4A at the first cross-sectional area. A cross-sectional area of a second slice SL2 is defined at a location is 20 mm proximal to the distal end of the tip. The second slice SL2 defines a plane perpendicular to the longitudinal axis L1, and the second slice SL2 is distal to the first slice SL1. FIG. 4C illustrates a sectional view of the ultrasonic tip of FIG. 4A at the second slice.

The cross-sectional area of the second slice SL2 is 5 to 6 times smaller than the cross-sectional area of the first slice SL1. In other words, the cross-sectional area of the second slice SL2 is 13-25, 15 to 21, 16-20, or 16.7-20% of the cross-sectional area of the first slice SL1. This results in an ultrasonic tip having a low gain. The low gain of the of the ultrasonic tip 20, which is calculated by dividing the ultrasonic tip 20 displacement by the ultrasonic handpiece 12 displacement, results in a reduction in stalling of the cutting portion 40 (e.g., cutting head 104), which improves performance of the ultrasonic tip 20 overall. It also requires drawing less power to drive the ultrasonic tip 20 and allows for driving the ultrasonic tip 20 at a higher current, which may improve cutting rate without an increase in stalling of the cutting portion 40 (e.g., cutting head 104).

For example and not by way of limitation, in the illustrated configuration, a diameter of the first slice SL1 is 8 mm, with a gun drill hole having a diameter of approximately 2 mm. In this configuration, the cross-sectional area of the first slice SL1 is approximately 47.1 $mm^2$. In some configurations, the cross-sectional area of the second slice SL2 may be approximately 8.725 $mm^2$. Thus, in this configuration, a value of the cross-sectional area of the second slice SL2 is approximately 5.4 times less than a value of the cross-sectional area of the first slice SL1.

In the illustrated configuration, the gain of the ultrasonic tip 20 is approximately 3. It should be appreciated that the ultrasonic tip 20 may exhibit a gain ranging between 2 and 5, 2 and 4, 2.5 and 3.5, and 2.75 and 3.25. Alternatively, the gain exhibited by the ultrasonic tip 20 may be below 5. By comparison, similar ultrasonic tips known in the art that are used for similar applications have a gain of approximately 7.0-7.4. The low gain of the of the ultrasonic tip 20, which is calculated by dividing the ultrasonic tip 20 displacement by the ultrasonic handpiece 12 displacement, results in a reduction in stalling of the cutting portion 40 (e.g., cutting head 104), which improves performance of the ultrasonic tip 20 overall. It also requires drawing less power to drive the ultrasonic tip 20 and allows for driving the ultrasonic tip 20 at a higher current, which may improve cutting rate without an increase in stalling of the cutting portion 40 (e.g., cutting head 104).

Gain could also be achieved by a uniform outer surface and is composed of two different materials longitudinally aligned with each other such as described in U.S. Pat. No. 9,962,183, entitled "Ultrasonic Torsional Tissue Dissection Utilizing Subaltern Modes of Longitudinal-Torsional Resonators", which is hereby incorporated by reference in its entirety.

The ultrasonic tip 20 may be free of a longitudinal to torsional motion conversion mechanism, and as such, configured to vibrate solely in the longitudinal direction. The ultrasonic tip 20 may consist of titanium.

The irrigation sleeve 18 described herein may be used with any type of ultrasonic tip. In other words, the irrigation sleeve 18 described herein may be used with ultrasonic tips that do not include the first and second bores 90, 92 described. In addition, the irrigation sleeve 18 described herein may be used with ultrasonic tips that do not having a cutting head that have two substantially planar sides. For example, the irrigation sleeve 18 described herein may be used with ultrasonic tips that have cylindrical shapes and that rely on longitudinal, torsion, or longitudinal and torsional motion, such as those described in United States Patent Publication No. 2005/0177184, U.S. Pat. No. 8,512, 340, United States Patent Publication No. 2008/0208231, which are each hereby incorporated by reference in their entirety.

The instrument described herein may be used with any of the tip configurations and/or any of the irrigation sleeve configurations described herein.

Clauses for additional protection:

I. An ultrasonic tip comprising a shaft and a cutting portion, said ultrasonic tip comprising:
  - a first side that is substantially planar extending from a proximal end to a distal end,
  - a second side that is substantially planar and disposed opposite the first side, and extending from the proximal end to the distal end, and
  - a cutting head disposed at the distal end,
  - a first bore defining an air inlet disposed proximal to the cutting head, and
  - a second bore extending from the proximal end of the shaft to the first bore.

II. The ultrasonic tip of clause I, wherein the cutting head exhibits a base portion having a transverse dimension between the first side and the second side, the transverse dimension extending perpendicular to the longitudinal axis of the cutting head, a tapered portion comprising a bevel and extending from the base portion to a cutting edge, said cutting edge comprising a length and having a U-shaped profile having a first leg portion, a second leg portion, and an arcuate shaped distal portion, wherein the first leg portion and the second leg portion are parallel to one another.

III. The ultrasonic tip of clause I or II, wherein
  - a cross-sectional area of a first slice of a largest circular cross-sectional area of the shaft defines a plane perpendicular to the longitudinal axis,
  - a cross-sectional area of a second slice of a smaller cross-sectional area at the proximal region of the shaft defines a plane perpendicular to the longitudinal axis, and
  - a value of the cross-sectional area of the second slice is 5.4 times less than a value of the cross-sectional area of the first slice.

IV. The ultrasonic tip of clause I, II, or III, further comprising an ultrasonic instrument having a proximal region and a distal region, said ultrasonic instrument comprising:
  - a housing comprising a proximal portion and a distal portion,
  - a transducer at least partially disposed within said housing,
  - a horn coupled to said transducer, and
  - said transducer coupled to a suction source by a first coupler, the ultrasonic tip coupled to the horn.

V. The ultrasonic tip of clause I, II, III, or IV, further comprising an irrigation sleeve, the irrigation sleeve comprising a body having a distal region and a proximal region, said body defining a helical groove which at least partially surrounds said shaft of said tip when the tip is in a lumen of the sleeve; and
  - a sheath coupled to and disposed over a portion of said body to surround at least a full revolution of the helical groove, said sheath having a proximal end and an opposing distal end,
  - an irrigation conduit disposed within said helical groove for conveying irrigation fluid,
  - the irrigation conduit further defining an inlet aperture disposed at the proximal region of said body, and an outlet aperture disposed at a distal region of said body, wherein the irrigation fluid enters the irrigation conduit at the inlet aperture and exits the irrigation conduit at the outlet aperture.

VI. An ultrasonic tip comprising: a shaft defining a longitudinal axis and a cutting portion, the ultrasonic tip defining a first side that is substantially planar and a second side that is substantially planar, the cutting portion further including a cutting head, the cutting head including a cutting edge, and wherein: the largest cross-sectional area of the tip defines a cross-sectional area of a first slice; a cross-sectional area of a second slice is defined at a location is 20 mm proximal to the distal end of the tip, the second slice and the first slice each being perpendicular to the longitudinal axis of the shaft, wherein the cross-sectional area of the second slice is 15-20% of the cross-sectional area of the first slice. In addition, in certain configurations, the tip features the largest cross-sectional are over a length of at least 20 mm. In other words, there is a section of the tip that has a constant cross-sectional area and that is equal to the largest cross-sectional area of the tip. Furthermore, in some instances, it should be appreciated that the tip may include a diameter of no larger than 9 mm to provide for optimal cutting of delicate bone.

VII. An ultrasonic tip comprising: a shaft defining a longitudinal axis and a cutting portion, the ultrasonic tip defining a first side that is substantially planar and a second side that is substantially planar, the cutting portion further including a cutting head, the cutting head including a cutting edge, and wherein: the largest cross-sectional area of the tip defines a cross-sectional area of a first slice; a cross-sectional area of a second slice is defined at a location is 20 mm proximal to the distal end of the tip, the second slice and the first slice each being perpendicular to the longitudinal axis of the shaft, wherein the cross-sectional area of the second slice is 5 to 6 times smaller than the cross-sectional area of the first slice. In addition, in certain configurations, the tip features the largest cross-sectional are over a length of at least 20 mm.

Several configurations have been discussed in the foregoing description. However, the configurations discussed herein are not intended to be exhaustive or limit the invention to any particular form. For example, while the example configurations describe the surgical instrument as an ultrasonic handpiece, it is further contemplated that the features and concepts described with regard to the ultrasonic handpiece may be applied to other medical or surgical instruments. This similarly applies to the ultrasonic tip, which may further include blades, drill bits, rotating burs, open-window shavers, and the like. The terminology which has been used is intended to be in the nature of words of description rather than of limitation. Many modifications and variations are possible in light of the above teachings and the invention may be practiced otherwise than as specifically described.

What is claimed is:

1. An ultrasonic surgical assembly to provide air cooling of an ultrasonic tip, the ultrasonic surgical assembly comprising:
- an ultrasonic tip comprising a shaft and a cutting portion, said ultrasonic tip comprising:
  - a first side that is substantially planar extending from a proximal end to a distal end,
  - a second side that is substantially planar and disposed opposite the first side, and extending from the proximal end to the distal end, the cutting portion including a cutting head disposed at the distal end, and the ultrasonic tip removably coupled to a horn, wherein said shaft further comprises a longitudinal axis; and an irrigation sleeve having a distal region and a proximal region and defining a lumen extending along the longitudinal axis, said irrigation sleeve at least partially surrounding said shaft and defining an inlet aperture, said irrigation sleeve further comprising:

a first conduit in fluid communication with the lumen, the first conduit having an outlet aperture, wherein said first conduit is configured for being connected to a liquid source;

the ultrasonic tip further comprising:

a sealing member coupled to an outer surface of said ultrasonic tip, the ultrasonic tip defining:

a first bore defining an air inlet disposed proximal to the sealing member, and a second bore extending from the proximal end of the shaft to the first bore to form a fluid path between the first bore and the second bore.

2. The ultrasonic surgical assembly of claim 1, further comprising an ultrasonic instrument configured for coupling to the ultrasonic tip and the irrigation sleeve, and wherein said irrigation sleeve further comprises a third bore proximal the first bore when the irrigation sleeve and the ultrasonic tip are coupled to the ultrasonic instrument.

3. The ultrasonic surgical assembly of claim 1, wherein said ultrasonic tip further defines a groove, and wherein said sealing member is disposed around said groove.

4. The ultrasonic surgical assembly of claim 1, wherein said first bore is perpendicular to an axis of said second bore.

5. The ultrasonic surgical assembly of claim 1, wherein said ultrasonic tip further comprises:

a base for coupling to a transducer and a body extending from the base, the body comprising the shaft and the cutting portion, wherein the body is coupled to the base at the shaft and said body extends from said shaft to said cutting portion along the longitudinal axis; and wherein the cutting head comprises a base portion and a tapered portion.

6. The ultrasonic surgical assembly of claim 5, wherein:

said base portion has a transverse dimension between the first side and the second side, the transverse dimension extending perpendicular to the longitudinal axis, and said tapered portion comprises a bevel and extends from the base portion to a cutting edge, said cutting edge comprising a length and having a U-shaped profile having a first leg portion, a second leg portion, and an arcuate shaped distal portion, wherein the first leg portion and the second leg portion are parallel to one another and each comprises a plurality of cutting teeth, wherein no more than one half of the length of the cutting edge comprises the plurality of cutting teeth at the distal end, and wherein the arcuate shaped distal portion is free from the plurality of cutting teeth.

7. The ultrasonic surgical assembly of claim 1, wherein said shaft of said ultrasonic tip is free of a lumen in the distal end.

8. An ultrasonic surgical assembly to provide air cooling of an ultrasonic tip, the ultrasonic surgical assembly comprising:

an ultrasonic instrument having a proximal region and a distal region, said ultrasonic instrument comprising:

a housing comprising a proximal portion and a distal portion, a transducer at least partially disposed within said housing, a horn coupled to said transducer, and said transducer configured to be coupled to a suction source by a first coupler;

an ultrasonic tip comprising a shaft and a cutting portion, the ultrasonic tip removably coupled to said horn by a tip coupler, wherein said shaft comprises a longitudinal axis;

an irrigation sleeve having a distal region and a proximal region and defining a lumen, said irrigation sleeve at least partially surrounding said shaft and defining an inlet aperture configured to receive irrigation liquid from an irrigation source, said irrigation sleeve further comprising:

a first conduit in fluid communication with the lumen, the first conduit configured to convey irrigation liquid from the inlet aperture to an outlet aperture; and a sealing member positioned between an outer surface of said ultrasonic tip and an inner surface of said lumen;

the ultrasonic tip defining:

a first bore defining an air inlet disposed proximal to the sealing member when the irrigation sleeve and the ultrasonic tip are coupled to the ultrasonic instrument, and a second bore extending from a proximal end of the ultrasonic tip to the first bore, said second bore in communication with the suction source through the tip coupler;

the irrigation sleeve defining a third bore proximal the first bore when the irrigation sleeve and the ultrasonic tip are coupled to the ultrasonic instrument, and wherein the ultrasonic surgical assembly defines a path to draw air from an ambient environment through the third bore, then through the first bore, and back through the second bore before the air exits the ultrasonic surgical assembly at the first coupler.

9. The ultrasonic surgical assembly of claim 8, wherein said ultrasonic tip further defines a groove, and wherein said sealing member is disposed around said groove.

10. The ultrasonic surgical assembly of claim 8, wherein said first bore is perpendicular to an axis of said second bore.

11. The ultrasonic surgical assembly of claim 8, wherein said ultrasonic tip further comprises:

a base for coupling to the transducer and a body extending from the base, the body comprising the shaft and the cutting portion, wherein the body is coupled to the base at the shaft and said body extends from said shaft to said cutting portion along the longitudinal axis; and wherein the cutting portion comprises a base portion and a tapered portion.

12. The ultrasonic surgical assembly of claim 11, wherein the ultrasonic tip further comprises:

a first side that is substantially planar extending from a proximal end to a distal end, and a second side that is substantially planar and disposed opposite the first side, and extending from the proximal end to the distal end.

13. The ultrasonic surgical assembly of claim 12, wherein:

said base portion has a transverse dimension between the first side and the second side, the transverse dimension extending perpendicular to the longitudinal axis, and said tapered portion comprises a bevel and extends from the base portion to a cutting edge, said cutting edge comprising a length and having a U-shaped profile having a first leg portion, a second leg portion, and an arcuate shaped distal portion, wherein the first leg portion and the second leg portion are parallel to one another and each comprises a plurality of cutting teeth, wherein no more than one half of the length of the cutting edge comprises the plurality of cutting teeth at the distal end, and wherein the arcuate shaped distal portion is free from the plurality of cutting teeth.

14. The ultrasonic surgical assembly of claim 8, wherein said shaft of said ultrasonic tip is free of a lumen in the distal end.

15. A method of cutting bone with an ultrasonic tip, the method comprising:

providing an ultrasonic tip comprising a shaft and a cutting portion, the ultrasonic tip removably coupled to a horn by a tip coupler, the horn coupled to a transducer, and the transducer coupled to a suction source by a first coupler; wherein the shaft comprises a longitudinal axis, the ultrasonic tip defining a first bore defining an air inlet and a second bore extending from a proximal end of the ultrasonic tip to the first bore, the first bore being transverse to the second bore, the second bore in communication with the suction source via the tip coupler;

providing an irrigation sleeve having a distal region and a proximal region and defining a lumen, the irrigation sleeve at least partially surrounding the shaft and configured to be coupled to an irrigation source with an inlet aperture configured to receive irrigation liquid from the irrigation source, said irrigation sleeve defining a first conduit in fluid communication with the lumen, the first conduit configured to convey irrigation liquid from the inlet aperture to an outlet aperture; and providing a sealing member between the outer surface of said ultrasonic tip and an inner surface of the lumen of the irrigation sleeve, wherein the first bore is disposed proximal to said sealing member;

the method further comprising:

drawing air via the suction source through the second bore and the first bore to cool the ultrasonic tip.

16. The method of claim 15, further comprising:

drawing one of smoke and an air-borne particulate through the first bore and through the second bore.

17. The method of claim 15, further comprising:

aspirating air through the first bore to the second bore to cool the ultrasonic tip.

18. The method of claim 15, further comprising:

wherein the sealing member is coupled to an outer surface of said ultrasonic tip.

19. The method of claim 15, further comprising:

providing a third bore defined in the irrigation sleeve, wherein the third bore is proximal the first bore when the irrigation sleeve and the ultrasonic tip are coupled to a handpiece, and aspirating air from an ambient environment through the third bore, then through the first bore, and back through the second bore.

* * * * *